(12) United States Patent
Januario et al.

(10) Patent No.: US 6,395,281 B1
(45) Date of Patent: May 28, 2002

(54) COSMETIC SKIN CONDITIONING COMPOSITIONS CONTAINING RED YEAST RICE EXTRACT

(75) Inventors: Thomas Eugene Januario, Middletown, NY (US); Uma Santhanam, Tenafly, NJ (US); Sreekumar Pillai, Wayne, NJ (US); Manisha Narayan Mahajan, Westwood, NJ (US); John Steven Bajor, Ramsey, NJ (US)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/737,072

(22) Filed: Dec. 14, 2000

Related U.S. Application Data
(60) Provisional application No. 60/170,669, filed on Dec. 14, 1999.

(51) Int. Cl.[7] .......................... A61K 35/78; A61K 6/00; A61K 31/34; A01K 37/00
(52) U.S. Cl. .................. 424/195.16; 424/401; 514/474; 514/557
(58) Field of Search ............................. 424/195.16, 448, 424/401; 514/474, 557

(56) References Cited

U.S. PATENT DOCUMENTS

| | | | |
|---|---|---|---|
| 4,996,196 A | | 2/1991 | Mitsuhashi et al. ............ 514/53 |
| 5,627,068 A | | 5/1997 | Kujumdzieva et al. .. 435/254.1 |
| 5,686,065 A | * | 11/1997 | Haney et al. |
| 5,801,192 A | * | 9/1998 | Dumas et al. |
| 5,955,092 A | * | 9/1999 | Granger et al. |
| 6,180,133 B1 | * | 1/2001 | Quan et al. |
| 6,180,670 B1 | * | 1/2001 | Duffy et al. |

FOREIGN PATENT DOCUMENTS

| | | | |
|---|---|---|---|
| EP | 542 398 | | 5/1993 |
| JP | 1090109 | * | 9/1989 |
| WO | 99/23996 | | 5/1999 |

OTHER PUBLICATIONS

Derwent Abstract of JP 6065038—published Mar. 8, 1994.
Derwent Abstract of JP 4210615—published Jul. 31, 1992.
Derwent Abstract of JP 1090109—published Apr. 6, 1989.
Derwent Abstract of JP 10194928—published Jul. 28, 1998.
Maturitas 19, Journal of the Climacteric & Postmnopause, "*Effect of a conjugated oestrogen (Premarin®) cream on ageing facial skin, A comparative study with a placebo cream*", P. Creidi et al., p. 211–223 (1994).
PCT International Search Report in a PCT application PCT/EP 00/11355.
Derwent Abstract of Japanese Patent JP 09 077634—published Mar. 3, 1997.
Derwent Abstract of Japanese Patent JP 11 169 162—published Jun. 29, 1999.

* cited by examiner

Primary Examiner—Christopher R. Tate
Assistant Examiner—Randall Winston
(74) Attorney, Agent, or Firm—Ellen Plotkin

(57) ABSTRACT

Cosmetic methods and compositions for conditioning human skin by topical application to the skin of cosmetic compositions containing red yeast rice extract. Cosmetic compositions containing red yeast rice extract in combination with ascorbyl palmitate, or sodium ascorbyl phosphate, or retinol, or retinyl ester are also disclosed.

4 Claims, No Drawings

COSMETIC SKIN CONDITIONING COMPOSITIONS CONTAINING RED YEAST RICE EXTRACT

This application claims the benefit of U.S. provisional application No. 60/170,669 filed Dec. 14, 1999.

FIELD OF THE INVENTION

Cosmetic methods and compositions for conditioning human skin by topical application to the skin of cosmetic compositions containing red yeast rice extract.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin. Consumers also frequently seek other benefits in addition to anti-aging. A frequent, undesirable skin condition is "oily skin," the condition which results from the excessive amount of sebum on the skin. Sebum is skin oil which is produced by sebocytes (cells of the sebaceous glands in the skin) and is then secreted to the skin surface. Oily skin is associated with a shiny, undesirable appearance and a disagreeable tactile sensation. Oily skin affects various age groups. Cosmetic actives which are able to provide both anti-aging benefits and sebum control are highly desirable, both from the manufacturer's and consumer's perspective.

In recent years, phytoestrogens (i.e., natural compounds which have estrogen-like activity and which are found in plants) have been increasingly used for cosmetic and therapeutic purposes. Estrogens and synthetic compounds which act like estrogens are known to increase the thickness of the dermal layer and reduce wrinkle formation in the aging skin. Changes in the skin such as skin dryness, loss of skin elasticity and plumpness occurring after menopause are attributed to the lack of estrogen production. Estrogen therapy prevents or slows down many of the changes associated with aging skin (Creidi et al., Effect of a conjugated oestrogen cream (Premarin®) on aging facial skin, Maturitas, 19, p. 211–23, 1994).

Red yeast rice is also known as Monascus sp. Prior art describes a melanin-formation inhibitor in skin care comprising pigment obtained by culturing Monascus mould (JP 6065038 A). Monascus chitinase has been used to prepare chitosan derivatives with tyrosinase inhibiting activity (JP 4210615 A). Cultured extract of the monascus fungus has been claimed in cosmetic material for skin cleansing (JP 1090109 A) and cosmetics for make-up (JP 10194928). U.S. Pat. No. 4,996,196 mentions red yeast rice used in a dehydration process of hydrous matter.

None of the art described above discloses anti-sebum or estrogenic properties of red yeast rice, or any cosmetic compositions containing red yeast rice in combination with acorbates or retinoids presently claimed.

SUMMARY OF THE INVENTION

The present invention includes a skin conditioning composition comprising:
(a) from about 0.001 to about 20 wt. % of red yeast rice extract;
(b) a co-active compound selected from the group consisting of ascorbyl palmitate; sodium ascorbyl phosphate, retinol, retinyl ester, and mixtures thereof; and
(c) a cosmetically acceptable vehicle.

The invention also includes a cosmetic method of controlling oily skin condition and of reducing, preventing or controlling sebum secretion from sebocytes by applying either the red yeast rice extract alone, or the inventive composition, to the skin.

The invention also includes a cosmetic method of stimulating collagen synthesis by fibroblasts in the skin, by applying either the red yeast rice extract alone, or the inventive composition, to the skin.

The invention also includes a cosmetic method of improving the appearance of wrinkled, lined, dry, flaky, aged or photodamaged skin and improving skin thickness, elasticity, flexibility and plumpness by applying either the red yeast rice extract alone, or the inventive composition, to the skin.

The invention also includes a cosmetic method of delivering a phytoestrogen to skin by applying to the skin a cosmetic composition comprising a red yeast rice extract in a cosmetically acceptable vehicle.

The inventive methods and compositions provide control of sebum secretion from sebocytes, improved oil control and improved skin feel, prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

The inventive compositions contain an extract of red yeast rice. Preferably the extract is an organic solvent extract. The organic extracts are prepared by extracting the red yeast rice powder with a solvent by stirring 1 part of red yeast rice with 2 to 5 parts of the solvent for from 4 to 24 hours at room temperature. Suitable solvents are described hereinbelow. The extracts are clarified by filtration and/or centrifugation, then used as is or dried by evaporation (optionally, under vacuum).

Solvents suitable for the preparation of red yeast rice extract for use herein include, but are not limited to: ethanol, butylene glycol, ethylene glycol, propylene glycolmethanol, hexane, chloroform, dichloromethane, DMSO (dimethylsulfoxide) and ethyl acetate. The preferred solvents are dichloromethane, methanol, or ethanol, or DMSO, or glycol:ethanol mixtures in order to maximize activity. The extract may be further concentrated, fractioned, re-extracted or purified, e.g. by organic solvent extraction or by chromatography.

The red yeast rice extract is employed in the present invention in an amount from 0.001 to 20 wt. %, preferably from 0.01 to 10 wt. %, most preferably from 0.01 to 5 wt. %.

Red yeast rice may be obtained from Shangai International Greenmen Trading Company.

According to one aspect of the invention, red yeast rice extract is employed in a variety of cosmetic methods: to deliver estrogenic activity to the skin; to control sebum secretion or oily skin, and to stimulate collagen production by fibroblasts.

According to another aspect of the invention, red yest rice extract is employed in combination with a co-active compound, in order to obtain substantially improved performance. The co-active compound is selected from the group consisting of ascorbyl palmitate; sodium ascorbyl phosphate, retinol, retinyl ester, and mixtures thereof. The preferred co-active compounds are sodium ascorbyl phosphate (due to its chemical stability) or trans-retinol.

The co-active compound may be obtained from Sigma Chemical Co. or BASF.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are C1–C30 esters of retinol, preferably C2–C20 esters, and most preferably C2, C3, and C16 esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadecanoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

The preferred ester for use in the present invention is selected from retinyl palmitate, retinyl acetate, retinyl linoleate and retinyl propionate, because these are the most efficaceous or the most commercially available and therefore the cheapest.

The co-active compound-is employed in the inventive compositions and methods generally in an amount of from 0.001 to 20 wt % preferably from 0.01 to 10 wt %, most preferably from 0.01 to 5 wt. %.

Cosmetically Acceptable Vehicle

The composition according to the invention also comprises a cosmetically acceptable vehicle to act as a dilutant, dispersant or carrier for the actives in the composition in the composition, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm$^2$/s (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, the amount of water is at least 50 wt. % of the inventive composition, most preferably from 60 to 80 wt. %, by weight of the composition. The preferred compositions are oil-in-water emulsions, containing at least 60%, preferably at least 80% water.

Optional Skin Benefit Materials and Cosmetic Adjuncts

The inventive compositions preferably include sunscreens to lower skin's exposure to harmful UV rays.

Sunscreens include those materials commonly employed to block ultraviolet light. Illustrative compounds are the derivatives of PABAI cinnamate and derivatives of salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

An oil or oily material may be present, together with an emollient to provide either a water-in-oil emulsion or an oil-in-water emulsion depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate,. diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20%. by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507 (silicone-based anhydrous composition within a gelatine capsule), incorporated by reference herein. The invention accordingly also provides a closed container containing a cosmetically acceptable composition as herein defined.

The following specific examples further illustrate the invention. Red yeast rice for the following experiments was purchased from Shanghai Greenmen International Trading Co. Red yeast rice extract was prepared by adding 1 ml ethanol to 1 mg of red yeast rice powder, warming it at 37° C. for 10 minutes, letting the powder settle and testing the supernatant (Example 1). Alternately, Red yeast rice extract was prepared by mixing 100 mg of the dry red yeast powder with 1 ml of a mix of DMSO: ethanol (10:90 v/v) to get a 10% solution. The solution was warmed to 40° C. for 2 hrs, vortexed, and then filtered and diluted for the test (Examples 2 and 3).

EXAMPLE 1

This example measured production of procollagen I by fibroblasts in response to treatment with various test compounds.

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643); and some correction in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with trefinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Methodology for determination of (Pro) Collagen-I protein expression using Dot Blot technique:

Cell Culture method:

Neonatal human dermal fibroblasts (passage 4 to 8) were purchased from Clonetics Corp. San Diego, Calif. All materials for cell culture were purchased from Life technologies, New York and used in passages 5–10. Cells were seeded at a density of approximately 7,500/well in the inner 48 wells of a 96-well plate in DMEM (Dulbecco's Modified Eagle's Medium), high glucose supplemented with 2 mM L-glutamine, 10% fetal bovine serum, and antibiotic and. antimycotic solutions. Cells were grown to confluence and washed with serum free, phenol red free DMEM and cells dosed with 200 $\mu$l actives in media. Each dosing was replicated in a total of six to twelve wells. Test compounds were used at concentrations as indicated in tables below. After 24 hours, the test compound solution or the control solution was removed and cells re-dosed with 100 $\mu$l actives in media. After 24 hours incubation, remove media and store at 4° C. with protease inhibitor (Aprotinin 1:200) until further use. The test compound solution was then diluted in 1X Tris buffered saline (pH=8) buffer (approximately 20 $\mu$l media in 200 $\mu$l buffer).

Dot Blot Technique:

PVDF membrane soaked in methanol and 2 filter papers in 1X TBS (pH=8). Bio-Rad dot blot apparatus was set up with filter paper on bottom, membrane on top, tighten, added 100 $\mu$l TBS per well. Vacuum dry. Vortex or mix, then load 100 $\mu$l diluted sample per well; let it sit for 15 minutes and then vacuum dry. Remove membrane from the apparatus, cut off excess, and notch bottom right corner for orientation. Place membrane in blocking buffer (5% milk powder in 1X TBS-Tween) for 1 hour at room temperature with shaking. Incubate for 1.5 hours at RT or overnight at 4° C. with 3 ml Rat Anti-Human Procollagen amino terminal antibody (Chemicon MAB1912) at 1:100 in 1% milk in TBS-T in a sealed bag with shaking. Remove membrane, do a 10 minute wash three to five times in TBS/0.1% Tween. Incubate for 1 hour at RT or O/N at 4° C. in 5 ml 1:1000 anti-rat conjugated alkaline phosphatase (AP) secondary antibody in 1-% milk in TBS-T in a sealed bag with shaking. Wash membrane for 15 minutes five to eight times with TBS-T, and final rinse with 1X PBS. The membrane was developed using Chemiluminiscent substrate (Boehringer Mannheim, Ind.) and results were analysed using a laser densitometer (Bio-Rad instrument). Fold increase was calculated as a ratio of densitometer reading for cells treated with a test compound over control.

The results that were obtained are summarized in Table 1.

TABLE 1

|  | Procollagen 1 production | % of Control | P value vs Control | Vitamin C/ Derivative | P value vs P value vs Red yeast rice |
|---|---|---|---|---|---|
| Control | 0.748 +/− 0.26 | 100 +/− 35 | 1 |  |  |
| Vitamin C(50 $\mu$g) | 1.311 +/− 0.28 | 175 +/− 37 | 0.005 | 1 |  |

TABLE 1-continued

| | Procollagen 1 production | % of Control | P value vs Control | Vitamin C/ Derivative | P value vs P value vs Red yeast rice |
|---|---|---|---|---|---|
| Ascorbyl Palmitate(50 µg) | 0.775 +/− 0.36 | 103 +/− 48 | 0.887 | 1 | |
| Sodium ascorbyl phosphate(50 µg) | 0.871 +/− 0.2 | 116 +/− 27 | 0.389 | 1 | |
| Red Yeast Rice 0.0001% | 2.265 +/− 0.47 | 302 +/− 64 | 0.000 | | 1 |
| Red Yeast Rice 0.0001% = Vitamin C | 0.172 +/− 0.04 | 22 +/− 5 | 0.000 | 0.000 | 0.000 |
| Red Yeast Rice 0.0001% = Ascorbyl Palmitate | 2.04 +/− 1.16 | 272 +/− 155 | 0.027 | 0.034 | 0.677 |
| Red Yeast Rice 0.0001 = Sodium Ascorbyl phosphate | 2.53 +/− 1.4 | 338 +/− 187 | 0.014 | 0.018 | 0.671 |
| Red Yeast Rice 0.003% | 0.07 +/− 0.05 | 10 +/− 7 | 0.000 | | 1 |
| Red Yeast Rice 0.003% = Vitamin C | 1.2 +/− 1.7 | 160 +/− 234 | 0.547 | 0.88 | 0.148 |
| Red Yeast Rice 0.003% = Ascorbyl Palmitate | 2.83 +/− 1.14 | 379 +/− 152 | 0.001 | 0.002 | 0.000 |
| Red Yeast Rice 0.003% = Sodium Ascorbyl phosphate | 1.632 +/− 0.28 | 218 +/− 38 | 0.001 | 0.001 | 0.00 |

It can be seen from the results in Table 1 that red yeast rice alone, or in combination with ascorbyl palmitate or sodium ascorbyl phosphate, stimulated collagen production by fibroblasts.

EXAMPLE 2

This example investigated the phytoesrogenic activity of red yeast rice extract.

Estrogen Responsive Cell Line, ZR 75 Cells:

The ZR75 cell line is a ductal breast carcinoma cell line, originally isolated from malignant mammary epithelium of a sixty-three year old Caucasian female (10). The chromosome number is triploid and the trypsin-Giemsa banding patterns indicate a unique karyotype distinct from HeLa cells. While containing receptors for estrogen, insulin, progesterone and other hormones, ZR75 cells only respond through an increase in proliferation to estrogen and insulin. The cell line contains high affinity estrogen-specific receptors. Therefore, this cell line is used for testing estrogen-like activity.

To grow and maintain ZR75 cells, the most effective media is RPMI1640 media with ten percent fetal bovine serum (FBS), 100 units penicillin per milliliter and 100 units of streptomycin per ml. The media itself does not contain Phenol Red (a weak estrogen mimetic). The cells are split 1:2 once every week and seeded in 24 well plates at one hundred thousand cells per milliliter per well for the assay.

Assay for Estrogen Like Activity:

After growing for twenty-four hours, the media was removed, the cells were washed with PBS and one ml of RPMI 1640 without serum was readded. Different dilutions of the red yeast rice extract were then dosed directly into each well. After another twenty-four hours, one microCurie of [methyl-3H] thymidine was added to the media in each well. The media was removed after twenty-four hours to begin the thymidine uptake assay. The cells were-washed once in PBS, the PBS was removed completely and the cells were left on ice to incubate with one milliliter per well of 10% TCA for one half hour. The plates were washed three times with 5% TCA to remove all traces of thymidine which wasn't incorporated into the cells. Five hundred microliters of 0.1M sodium hydroxide was added to each well and the plates were incubated at 50° C. for 15 min. The samples were transferred to scintillation vials and after adding five milliliters of counting fluid (scintiverse), the vials were counted for five minutes each on a setting for tritium. Data from triplicate dishes were calculated as % thymidine incorporation into DNA compared to that of control wells which did not receive any actives. Each assay also included 10 nM of estradiol as a positive control. Data was calculated as % of control to normalize for experiment-to-experiment variation.

The results that were obtained are summarized in Table 2.

TABLE 2

| Groups | Concentration | cpm +/− SD | % of control |
|---|---|---|---|
| Control | 0 | 117579 +/− 7608 | 100 +/− 6.4 |
| Estradol | 0.27 × 10$^{-6}$% (10 nM) | 263982 +/− 711 | 224 +/− 6.0* |
| Red Yeast Rice | 0.01% | 345313 +/− 3275 | 293 +/− 2.8* |
| | 0.001% | 360195 +/− 4864 | 306 +/− 4.1* |
| | 0.0001% | 147358 +/− 6736 | 125 +/− 5.7 |
| | 0.00001% | 145873 +/− 3304 | 124 +/− 2.8 |

*- p less than 0.001.

It can be seen from the results in Table 2 that, at 0.01% and 0.001%, red yeast rice extract had estrogenic activity equivalent to or greater than that of 10 nM estradiol. Although red yeast rice extract is not as potent as estradiol, use of red yeast rice is advantageous because estradiol, being a drug, cannot be used in cosmetics whereas red yeast rice can be used in cosmetic products.

EXAMPLE 3

This example investigated the effect of various tested compounds on CRABP-2 production by fibroblasts.

Within the cells, retinol and retinoic acid are bound to specific cellular binding proteins, 2 of the major proteins are CRABP-1 and 2 (Roos et al., Pharmacological reviews: 50, 315–333, 1998). These proteins act in regulating the intracellular concentration of retinoids by acting as both storage or shuttle proteins in retinoid metabolism. High or low levels of retinoids cause cell damage, including cell death, therefore regulation of constant levels of retinoids and its binding proteins are very critical for cell survival. The levels of this protein are re gulated by the amount of retinoic acid within the cells. Higher cellular levels of retinoids increase the expression of CRABP-2. Therefore, the amount of this protein in the cells, is a measure of the retinoid activity of the cells. Skin cells contain CRABP-2 both in the epidermis and the dermis. CRABP-2 response to retinoid administration in fibroblasts in vitro is used as a reproducible measure of retinoid bioactivity that predict human skin responses (Elder et aI., J. Invest. Dermatol., 106: 517–521, 1996).

Cell Culture Method for Fibroblasts:

Human adult fibroblasts obtained from su n-protected inner arm of 25–30 year female volunteer were used in this. Cells were grown in 1:1 DMEM/Hams F12 media containing 10% FBS, maintained at 37° C. in a 5% CO2 atmosphere under normal atmospheric oxygen tension. Third passage adult fibroblasts were grown in DMEM media with 10% FBS in 12-well plates at a seeding density of 2500 cells/ml/well. The cells at 80% confluence were rinsed in serum free and phenol red free (PRF) DMEM media twice. Pretreatment with test compound for 4 hours was conducted and then dosed with retinoids and was incubated for 48 hours.

Detection of Cellular Retinoic Acid Binding Protein 2 (CRABP-2) in Fibroblasts:

After the incubation, the wells were was ed twice with 1X PBS and the cell monolayer was harvested in 100 $\mu$l cell lysis buffer (contains 1X PBS, 1% TritonX, 0.5% sodium deoxycholate, 0.1% SDS containing p tease inhibitor (10 mg/ml PMSF in isopropanol, 10 $\mu$l/ml). The suspension was spun at 14000 rpm for 10 minutes, the supernatant collected and an aliquot of this supematant was used for protein quantification. Protein concentration was determined using Pierce protein kit. The remainder of 100 $\mu$l supernatant (cell lysate) was denatured in a mixture of 40 $\mu$l sample buffer (NOVEX) and 0.5% Beta mercaptoethanol (IBME) and by boiling the sample for 5 minutes. Equal amount of protein was then loaded onto 16% Tris-glycine gels for protein analysis by SDS page and Western Immuno-blotting for CRABP-2 protein expression.

The gels were run and transferred to nitrocellulose blots and Western Blotting was carried out using monoclonal antibodies to CRABP-2 according to standard procedures. The CRABP-2 protein band was visualized in the Western Blots using the chemiluminescence system obtained from Santa Cruz Biotechnology (SantaCruz, Calif.). The bands in the film were quantitated by densitometric scanning, the-data from triplicate samples were calculated as % of control and expressed in the following tables as % increase over control (with control as 100%) +/–SD of triplicates.

The results that were obtained are summarized in Table 3.

TABLE 3

|  | CRABP-2 OD +/– SD | CRABP-2 % of Control | P value vs Control | P value vs retinoids | P value vs Red yeast |
|---|---|---|---|---|---|
| Control | 1.25 +/– 0.30 | 100 +/– 24 | 1 | | |
| 10e-6M Retinol | 1.91 +/– 0.06 | 153 +/– 5 | 0.02 | 1 | |
| 10e-6M Retinyl linoleate | 1.96 +/– 0.16 | 156 +/– 13 | 0.02 | 1 | |
| 10e-6M Retinyl palmitate | 2.00 +/– 0.04 | 178 +/– 33 | 0.045 | 1 | |
| 10e-6M Retinyl Acetate | 3.86 +/– 0.28 | 398 +/– 157 | 0.0023 | 1 | |
| 0.1 $\mu$l Red Rice Yeast extract (RYR) | 1.29 +/– 0.04 | 102 +/– 3 | 0.84 | | 1 |
| 10e-6M Retinol = 0.001% RYR | 3.53 +/– 0.22 | 282 +/– 29 | 0.0011 | 0.00162 | 0.00045 |
| 10e-6M Retinyl linoleate = 0.001% RYR | 3.39 +/– 0.22 | 270 +/– 17 | 0.000605 | 0.000897 | 9.30E-05 |
| 10e-6M Retinyl palmitate = 0.001% RYR | 3.64 +/– 0.42 | 290 +/– 33 | 0.00133 | 0.01377 | 0.000641 |
| 10e-6M Retinyl Acetate = 0.001% RYR | 6.09 +/– 1.15 | 486 +/– 91 | 0.00215 | 0.083 | 0.00195 |

It can be seen from the results in Table 3 that red yeast extract by itself had no effect on CRABP-2 levels. Pretreatment for 4 hours with red yeast rice extract increased the efficacy of retinoids (retinol, retinyl palmitate, retinyl linoleate and retinyl acetate) to induce CRABP-2 protein levels.

EXAMPLE 4

This example investigated the effect of red yeast rice on sebum secretion by sebocytes.

Secondary cultures of human sebocytes obtained from an adult male were grown in 48-well tissue culture plates (Costar Corp.; Cambridge, Mass.) until confluent. Sebocyte growth medium consisted of Clonetics Keratinocyte Basal Medium (KBM) supplemented with 14 $\mu$g/ml bovine pituitary extract, 0.4 $\mu$g/ml hydrocortisone, 5 $\mu$g/ml insulin, 10 ng/ml epidermal growth factor, 1.2×10–10 M cholera toxin, 100 units/ml penicillin, and 100 $\mu$g/ml streptomycin. All cultures were incubated at 37° C. in the presence of 7.5% CO2. Medium was changed three times per week.

On the day of experimentation, the growth medium was removed and the sebocytes washed three times with sterile Dulbecco's Modified Eagle Medium (DMEM; phenol red free). Fresh DMEM was added to each sample (triplicates in Table 4 and duplicated in Table 5) with 5 microliter of test agent solubilized in ethanol. Controls consisted of addition of ethanol alone. Each plate was returned to the incubator for 20 hours followed by the addition of 14C-acetate buffer (5 mM final concentration, 56 mCi/mmol specific activity). Sebocytes were returned to the incubator for four hours after which each culture was rinsed three times with phosphate buffered saline to remove unbound label. Radioactive label remaining in the sebocytes was harvested and counted using a Beckman scintillation counter. Phenol Red was incorporated as an internal positive control.

The results that were obtained are summarized ion Tables 4 and 5.

TABLE 4

| Treatment | % Reduction | T-test |
|---|---|---|
| 0.001% Phenol Red | 83.4 | $7.9e10^{-6}$ |
| 0.01% Red Yeast Rice | 61.4 | 0.0008 |

TABLE 5

| Treatment | % Reduction | T-test |
|---|---|---|
| .00035% Phenol Red | 8.1 | 0.1437 |
| .0035% Phenol Red | 63.5 | 0.0246 |
| 0.001% Red Yeast Rice | 30.7 | 0.0007 |
| 0.0001% Red Yeast Rice | 0.5 | 0.7296 |

It can be seen from the results in Tables 4 and 5 that red yeast rice at concentrations 0.001% or higher significantly inhibited sebum production by sebocytes.

Example 5 illustrates topical compositions according to the present invention. The compositions can be processed in conventional manner. They are suitable for cosmetic use. In particular the compositions are suitable for application to wrinkled, rough, flaky, aged oily and/or UV-damaged skin and/or oily skin to improve the appearance and the feel thereof as well as for application to healthy skin to prevent or retard deterioration thereof.

| INGREDIENT | % w/w |
|---|---|
| OIL-IN-WATER EMULSION | |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Isopropyl Myristate | 5.00 |
| Octyl Palmitate | 3.00 |
| Cetyl Alcohol | 1.00 |
| Red Yeast Rice Extract | 0.10 |
| Sodium Ascorbyl Phosphate | 5.00 |
| Dimethicone, 100 cst | 0.50 |
| Beeswax | 0.30 |
| Propylparaben | 0.10 |
| Germall II | 0.10 |
| Fragrance | 0.10 |
| Dl Water | to 100% |
| Total → | 100.00 |
| OIL-IN-WATER EMULSION | |
| Xanthan Gum | 0.20 |
| Disodium EDTA | 0.10 |
| Glycerin | 5.00 |
| Butylene Glycol | 2.00 |
| Methylparaben | 0.30 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Red Yeast Rice Extract | 1.00 |
| Propylparaben | 0.10 |
| Germall II | 0.10 |
| Fragrance | 0.10 |
| Retinol | 0.075 |
| Dl Water | to 100% |
| Total → | 100.00 |
| WATER-IN-OIL EMULSION | |
| Disodium EDTA | 0.10 |
| Glycerin | 3.00 |
| Retinyl Acetate | 3.00 |
| Red Yeast Rice Extract | 3.00 |
| Propylene Glycol | 2.00 |
| Sodium Chloride | 0.70 |
| Methylparaben | 0.30 |
| Cyclomethicone | 14.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Dl Water | to 100% |
| Total → | 100.00 |
| HYDRO-GEL | |
| Butylene Glycol | 5.00 |
| PPG-5-Ceteth 20 | 5.00 |
| Glycerin | 3.00 |
| Ascorbyl Palmitate | 2.00 |
| Red Yeast Rice Extract | 2.00 |
| Retinyl Palmitate | 2.00 |
| Carbomer | 1.20 |
| Triethanolamine 99% | 1.20 |
| Methylparaben | 0.30 |
| Polysorbate 20 | 0.25 |
| Disodium EDTA | 0.10 |
| Germall II | 0.10 |
| Dl Water | to 100% |
| Total → | 100.00 |
| ANHYDROUS SERUM | |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Red Yeast Extract | 1.00 |
| All-Trans Retinol | 0.10 |
| Beeswax | 0.30 |
| Propylparaben | 0.20 |
| Fragrance | 0.10 |
| Cyclomethicone | to 100% |
| Total → | 100.00 |
| HYDRO-ALCOHOLIC GEL | |
| Alcohol SDA40B | 30.00 |
| Red Yeast Rice Extract | 5.00 |
| Butylene Glycol | 5.00 |
| PPG-5-Ceteth 20 | 5.00 |
| Sodium Ascorbyl $PO_4$ | 3.00 |
| Glycerin | 3.00 |
| Carbomer | 1.20 |
| Triethanolamine 99% | 1.20 |
| Methylparaben | 0.30 |
| Polysorbate 20 | 0.25 |

-continued

| INGREDIENT | % w/w |
|---|---|
| Disodium EDTA | 0.10 |
| Germall II | 0.10 |
| DI Water | to 100% |
| Total → | 100.00 |

What is claimed:

1. A cosmetic skin conditioning composition comprising:

(a) from about 0.001 to about 20 wt. % of organic solvent extract from Monascus;

(b) a co-active compound selected from the group consisting of ascorbyl palmitate, sodium ascrobyl phosphate, retinol, retinyl ester, and mixtures thereof; and (c) a cosmetically acceptable vehicle.

2. A cosmetic method of reducing, preventing or controlling sebum secretion from sebocytes by applying to the skin the composition of claim 1.

3. A cosmetic method of stimulating collagen synthesis by fibroblasts in the skin by applying to the skin the composition of claim 1.

4. A cosmetic method of improving the appearance of wrinkled, lined, dry, flaky, aged or photodamaged skin and improving skin thickness, elasticity, flexibility and plumpness by applying to the skin the composition of claim 1.

* * * * *